(12) United States Patent
Elliott

(10) Patent No.: US 7,737,321 B2
(45) Date of Patent: Jun. 15, 2010

(54) COLOSTOMY ALERT DEVICE AND METHOD

(76) Inventor: Nyle S. Elliott, 2727 Bens Branch Dr., #1302, Kingwood, TX (US) 77339

(*) Notice: Subject to any disclaimer, the term of this patent is extended or adjusted under 35 U.S.C. 154(b) by 1848 days.

(21) Appl. No.: 10/667,655

(22) Filed: Sep. 23, 2003

(65) Prior Publication Data

US 2005/0065488 A1   Mar. 24, 2005

(51) Int. Cl.
*A61B 19/00* (2006.01)
*A61M 31/00* (2006.01)
*A61M 1/00* (2006.01)
*G08B 21/00* (2006.01)
*G08B 23/00* (2006.01)

(52) U.S. Cl. .............. 604/361; 604/277; 604/318; 604/322; 604/338; 604/342; 604/333; 340/604; 340/612; 340/573.1; 200/61.04; 200/61.05; 200/61.19

(58) Field of Classification Search .............. 604/277, 604/318, 332, 338, 342, 333, 334, 336, 343, 604/175, 335, 337; 340/604, 612, 573; 200/61.04, 200/61.05, 61.19
See application file for complete search history.

(56) References Cited

U.S. PATENT DOCUMENTS

| 3,971,371 | A | * | 7/1976 | Bloom | 128/886 |
|---|---|---|---|---|---|
| 4,084,438 | A | * | 4/1978 | Lee et al. | 73/706 |
| 4,106,001 | A | * | 8/1978 | Mahoney | 340/604 |
| 4,121,589 | A | * | 10/1978 | McDonnell | 604/328 |
| 4,136,603 | A | * | 1/1979 | Doyle, Jr. | 92/98 R |
| 4,205,671 | A | * | 6/1980 | Lassen | 128/886 |
| 4,351,322 | A | * | 9/1982 | Prager | 600/32 |
| 4,781,176 | A | * | 11/1988 | Ravo | 600/30 |
| 4,813,422 | A | * | 3/1989 | Fisher et al. | 600/473 |
| 4,977,906 | A | * | 12/1990 | Di Scipio | 128/885 |
| 4,981,465 | A | * | 1/1991 | Ballan et al. | 600/32 |
| 5,036,859 | A | * | 8/1991 | Brown | 600/547 |
| 5,108,430 | A | * | 4/1992 | Ravo | 623/23.68 |
| 5,266,928 | A | * | 11/1993 | Johnson | 340/604 |
| 5,479,935 | A | * | 1/1996 | Essen-Moller | 600/547 |
| 5,568,128 | A | * | 10/1996 | Nair | 340/573.5 |
| 5,569,216 | A | * | 10/1996 | Kim | 604/277 |
| 6,171,289 | B1 | * | 1/2001 | Millot et al. | 604/336 |
| 6,350,255 | B1 | * | 2/2002 | von Dyck | 604/338 |
| 6,485,476 | B1 |   | 11/2002 | von Dyck et al. | |

(Continued)

OTHER PUBLICATIONS

Online dictionary: "ring" accessed Oct. 15, 2007. http://www.askoxford.com/concise_oed/ring_1?view=uk.*

*Primary Examiner*—Leslie R. Deak
*Assistant Examiner*—Adam Marcetich
(74) *Attorney, Agent, or Firm*—Hoffman, Wasson & Gitler

(57) ABSTRACT

A method and apparatus for alerting a colostomate or medical attendant to the presence of fecal matter. The device includes a hollow plug detachably securable to a flexible port positioned about the stoma. The port carries an alarm circuit which is triggered when fecal matter enters the plug lumen which will alert the colostomate to an impending episode. The signal may be vibratory, audible or visible and may be transmitted to a remote location. The device includes an inflatable air cuff which, when inflated, presents a physical barrier to the passage of fecal matter. Gas may pass through filters in the tube. The method involves positioning the device in the stoma, inflating the cuff and generating an alarm when matter is sensed.

15 Claims, 5 Drawing Sheets

U.S. PATENT DOCUMENTS

| | | | |
|---|---|---|---|
| 6,568,274 B1 * | 5/2003 | Lucas et al. | 73/718 |
| 6,617,488 B1 * | 9/2003 | Springer et al. | 604/361 |
| 6,723,040 B2 * | 4/2004 | Brady | 600/29 |
| 6,764,474 B2 * | 7/2004 | Nielsen et al. | 604/344 |
| 6,843,766 B1 * | 1/2005 | Nemir et al. | 600/31 |
| 2002/0019615 A1 * | 2/2002 | Roe et al. | 604/361 |

* cited by examiner

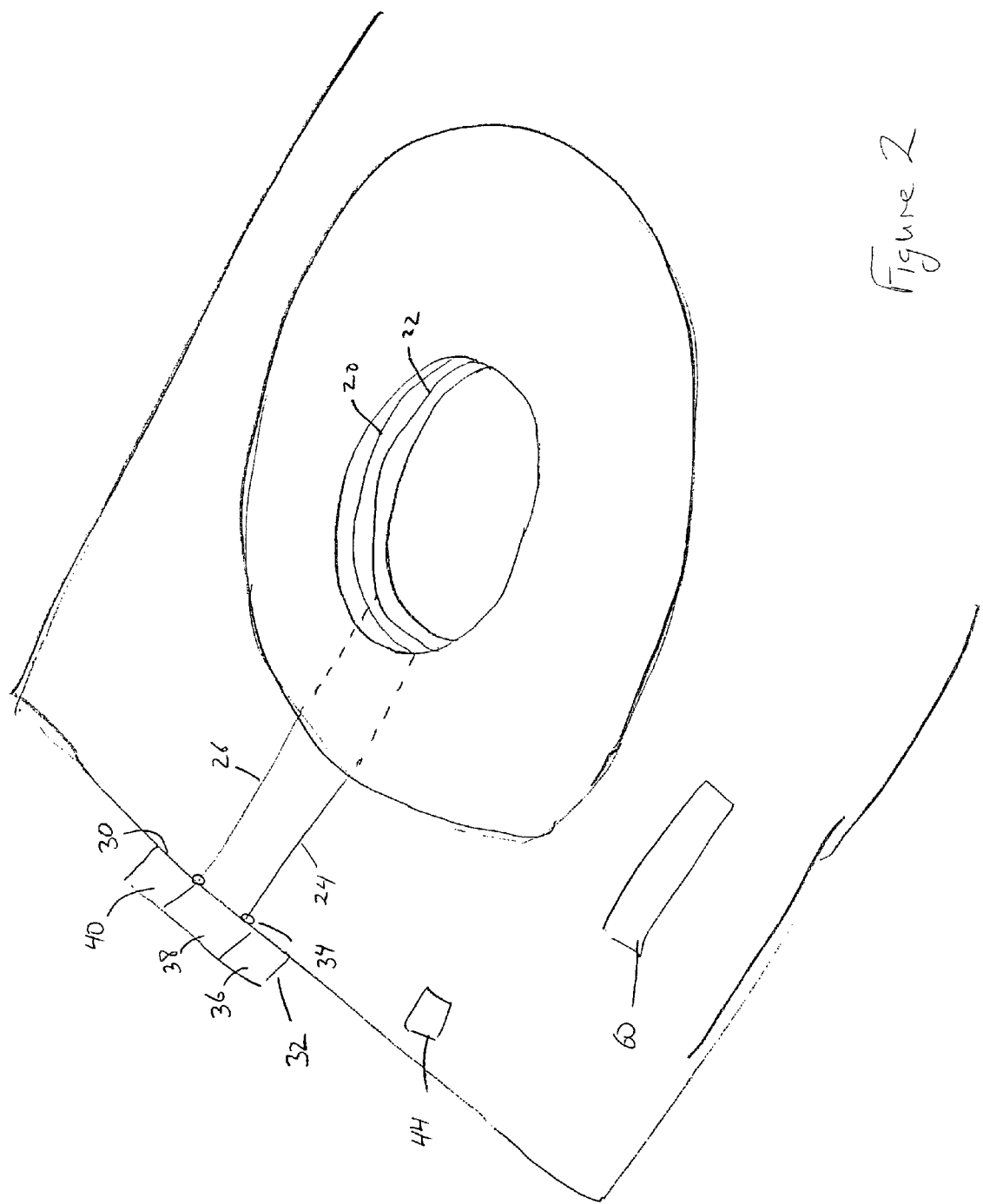

COLOSTOMY ALERT DEVICE AND METHOD

FIELD OF THE INVENTION

The present invention relates to a device and method for alerting an individual to enable the individual to better control fecal discharge and more particularly relates to an alert device and method for colostomy patients.

BACKGROUND OF THE INVENTION

Many patients, due to various medical conditions, have undergone diversionary colostomy procedures. A colostomy is a surgical creation of an artificial anus in the abdominal wall by incising the colon and then extending it to the surface. The stoma is the end of the small bowel extending through the abdomen. Colostomies are often performed because of cancer or benign, obstructive tumors or severe abdominal wounds. Many colostomates establish a regular schedule with proper care, colostomy irrigation and a proper pouching system.

However, even with proper surgery and post-surgical care, colostomates may suffer incontinence and lack the control over gas and feces that the normal rectal sphincter affords.

Accordingly, there exists a need for a device used by colostomy patients alerting the patient to an impending episode and also creating an obstacle or barrier to the passage of fecal matter. Review of the existing published art indicates there are various devices and methods for the detection, indication and prevention of such incontinent episodes.

U.S. Pat. No. 4,813,422 relates to a bowel control probe apparatus and method for sensing and preventing incontinent episodes. The probe comprises a catheter with an IP sensor tip for sensing fecal mass in the rectum and a cuff which is inflated with air to prevent passage of the fecal mass. The method of sensing and preventing incontinent episodes includes inserting the probe in the rectum, inflating the cuff, transmittion IR light into the rectum, monitoring the reflective IR light and generating an alarm signal when a predetermined amount of reflective IR is measured.

European Patent Application No. 88303054.6 also discloses a probe insertable into the colon having a sensor element at the tip and a light transmissive element. The sensor reflects light transmitted in response to the presence of fecal matter. The probe is preferably two-piece having a disposable section for insertion, inflatable cuff is provided to block the colon. Vent ports may be provided.

The preceding two patents relate to devices and methods for monitoring fecal mass in the colon. The patent literature also suggest other types of devices for use by colostomy patients. U.S. Pat. No. 4,351,322 relates to a stoma-control device and method including a support ring for surgical implantation in the body beneath the abdominal wall extending substantially around the stoma. The support is formed of a soft material and tapers outwardly to a large supporting surface for the bowel. A plug is adapted to be received in the stoma within the bowel for controlling the stoma. The plug includes an inflatable balloon which, when inflated, presents an outwardly tapered surface with a shape complimenting the tapered inner surface of the support.

U.S. Pat. No. 6,171,289 relates to a disposable device for securing a colostomy bag to a stoma which has an adhesive seal which is applied on the patient by means of a contact face. A through passage communicates with the stoma. A wetness detection device comprising at least two series of electrodes for measuring conductivity are provided to trigger an alarm when a predeteremined level of wetness is reached.

Thus, from the foregoing, it will be seen there are various approaches to providing comfort to individuals having bowel incontinence which includes use of optical wetness sensors. In the case of colostomy patients, the existing art suggests insertable devices including an inflatable element for blocking fecal matter. However, there nevertheless exists a need for a colostomy alert device which is comfortable and which will provide an obstacle to passage of fecal matter and which device does not require surgical implantation. There also exists a need for a device which will provide the user an indication of an impending episode so that the patient may, by having advance notification, take appropriate action to avoid any unpleasant and embarrassing incontinent episodes. In case of an ambulatory patient, the individual may remove himself or herself to a bathroom. In the case of a bedridden patient, the individual can summon a medical attendant prior to elimination so the individual may be assisted in reaching toilet facilities. Thus, elimination can be controlled in a manner which avoids both embarrassment and the soiling of clothing and bed linens.

SUMMARY OF THE INVENTION

The present invention provides an apparatus and method for monitoring the presence of fecal mass in a stoma and providing an alarm signal that will provide the user an indication of an impending episode. Further, the device and method of the present invention provides a physical barrier or obstacle to the passage of fecal matter from the bowel.

The alert system comprises a hollow plug and a pliable port adhesively attached about the stoma. The plug incorporates both a hydrophobic and an odor eliminating filter. The plug has a pair of electrical contacts which, when the plug is engaged in the port, are connected to a sensor. The contacts also are connected to a pair of contacts at the lower end of the plug. When fecal matter enters the plug and bridges the lower contact, a circuit is completed, activating the sensor to provide a tactile or audible alert. An inflatable cuff about the tube creates a barrier to passage of fecal matter. The plug may be removed, irrigated or replaced as necessary. A pouch system may be utilized without removing the slidable port so as to protect the patient's skin.

BRIEF DESCRIPTION OF THE DRAWINGS

FIG. 2 is a top view of the colostomy alert device of the present invention;

DETAILED DESCRIPTION OF THE INVENTION

Figure 1:
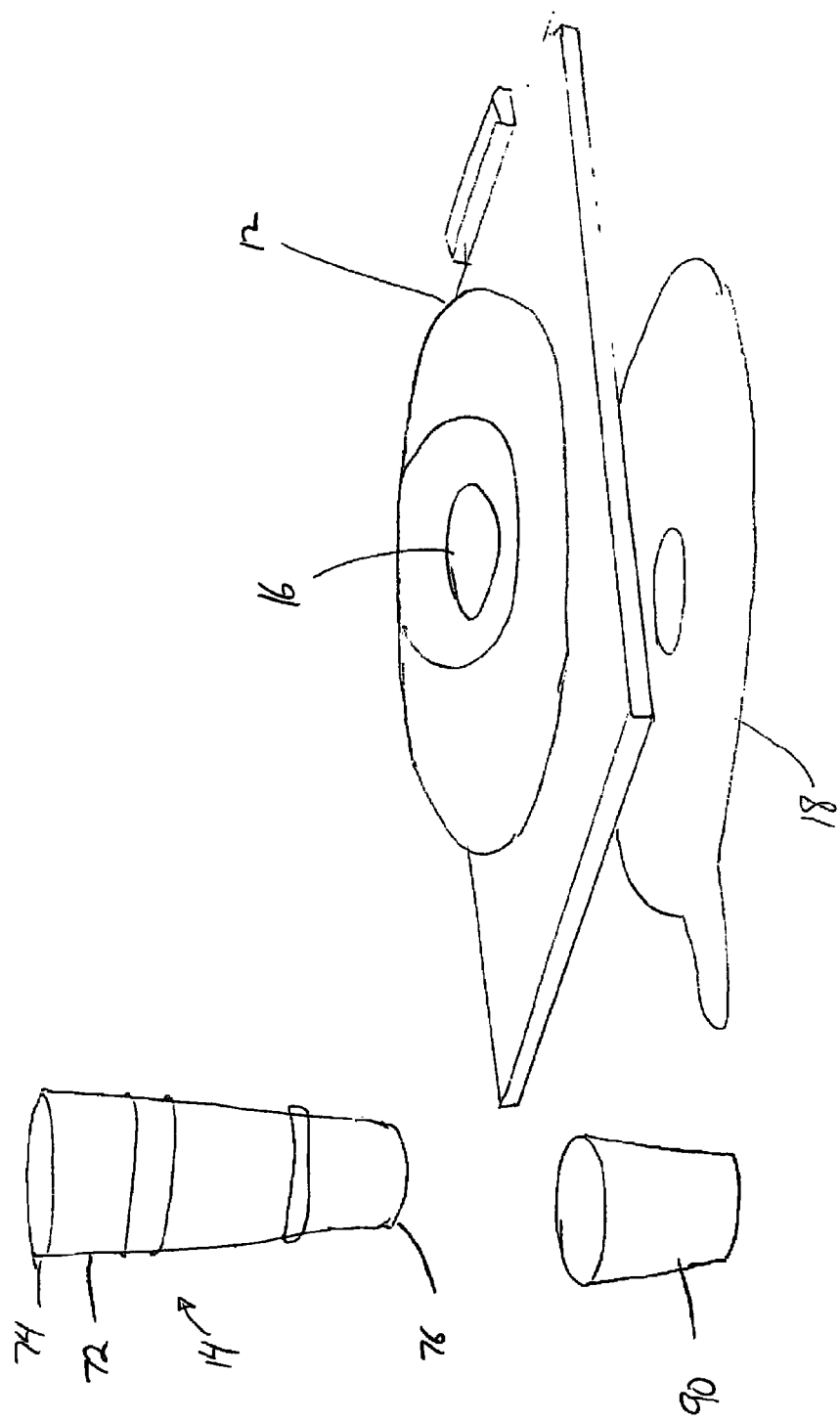
FIG. 1 is an exploded view of the colostomy alert device of the present invention.

The exploded view of FIG. 1 shows the components of the alert device. The device includes a pad 12 having a central aperture 16. The pad 12 is adhered to the patient by an adhesive ring 18, having a central aperture in registry with the aperture 16 of the pad 12. The central aperture 16 receives a plug 14. The plug 14 is formed by a lumen 72 having a top end 74 and bottom end 76. An absorbent sleeve 90 encircles the plug 14 to absorb any moisture. The sleeve is made of gauze or any other suitable material and may be removed and replaced as necessary.

The circuit board may have a replacement indicator. The replacement indicator counts elapsed time that the device has been used or the number of times the plug has been removed and replaced. Once a threshold limit of either of these measures has been reached, the circuit board will send a signal to an indicator for alerting the user to the fact that the entire device needs to be replaced. The periodic replacement of the device insures that the device will not fail due to a dead battery.

With reference to FIG. 2, the detail of the pad 12 can be seen. The pad has a central raised area, affording greater depth to the aperture 16. The sidewall of the aperture 16 houses conductive rings 20, 22. Each conductive ring is connected to a conductor 24, 26 leading from the central aperture to a location 30 on the edge of the pad. Attached to the terminal end of the conductors 24, 26 is circuit board 32. The circuit board may be permanently affixed to the pad or may be connected by suitable connectors 34 to the conductors 24, 26 to be maintained in place. The circuit board 32 contains a power source 36, such as a battery, an alarm 38 and a signaler 40, such as an LED. In addition to the circuit board 32, the pad can be provided with a transmitter 44 for sending a signal to a remote location such as medical attendants at a nearby nurses station. In place of or in addition to the signaler 40, the pad may include a tactile alarm, such as a vibrator 60. The vibrator 60 would derive its power from the battery 36 or may be provided with its own power source.

Figure 4:
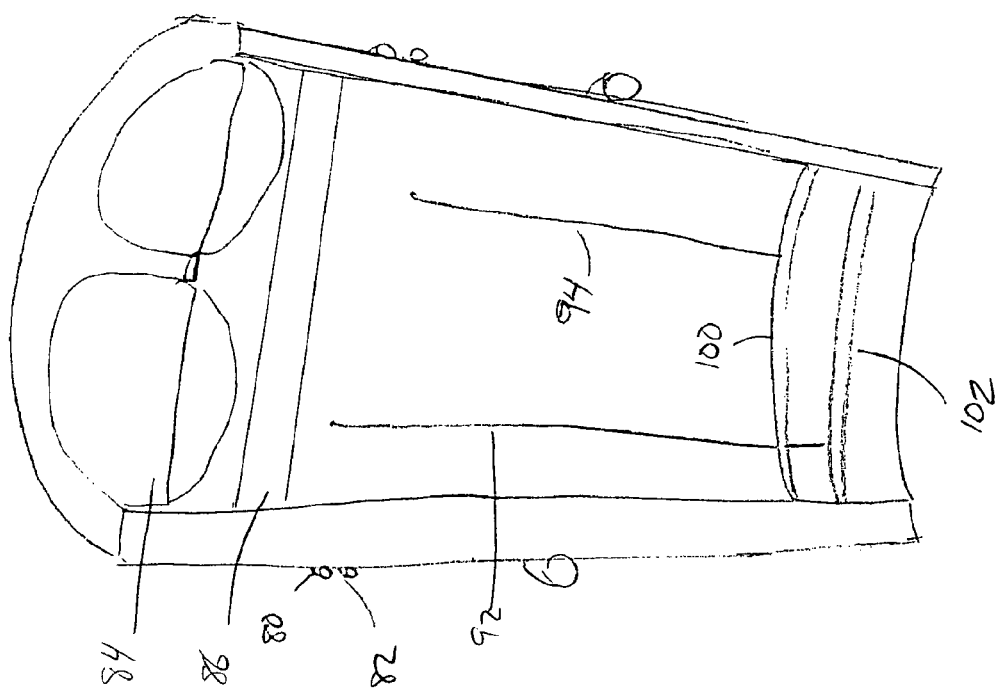
FIG. 4 is a cross-sectional view of the plug.
Figure 3:
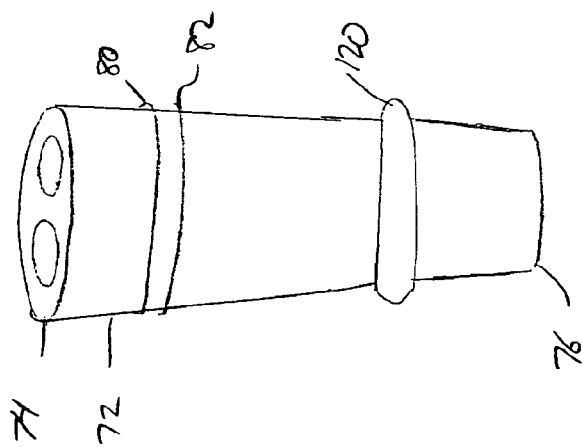
FIG. 3 is a perspective view of the plug.

The structure of the plug 14 is best seen with reference to FIGS. 3 and 4. In FIG. 3, located below the top end 74 are two conductive rings 80, 82 encircling the outer surface of the plug. When the plug is inserted into the central aperture of the pad, the top ring 80 makes contact with the upper ring 20. In a like manner, the lower ring 82 makes contact with the lower ring 82. The ring conductors could be other shapes such as strips or points, but the rings make alignment of the conductors easier. Also, about the outer surface of the plug is an inflatable cuff 120. When the plug is inserted into the stoma, the cuff can be inflated to help maintain the plug in place.

FIG. 4 shows the internal structure of the plug 14. Near the bottom end 76 of the plug, first and second conductors 100, 102 encircle the inner surface of the plug. Each lower conductive ring 100, 102 is electrically connected to an upper conductive ring 80, 82 by a conductor 92, 94. As depicted, lower conductive ring 102 is connected to upper conductive ring 80 by a first conductor 92 whereas lower conductive ring 100 is electrically connected to upper conductive ring 82 by a second conductor 94. Which lower ring is connected to which upper ring is not important as long as one of the upper rings is connected to one of the lower rings. Located at the top of the plug is a hydrophilic filter 82 and a charcoal filter 86. Combined, the filters allow the venting of gas to avoid bloating.

Figure 5:
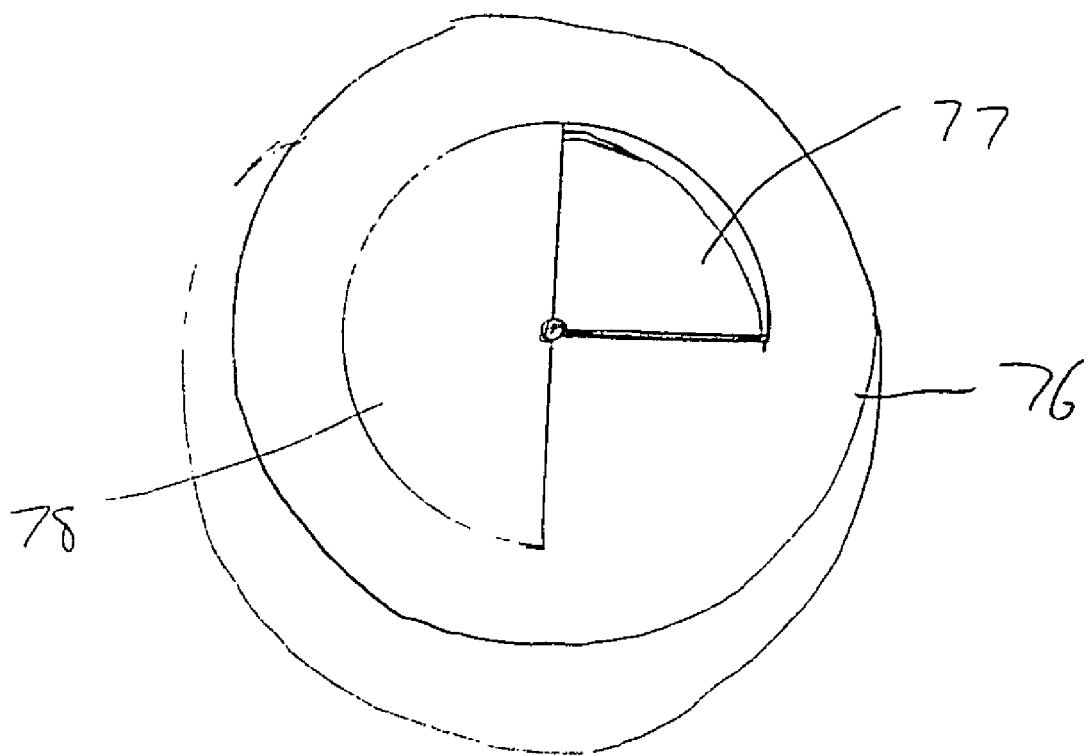
FIG. 5 is a perspective view of a plug having an adjustable opening.

The bottom of the plug 14 may be open as shown in FIG. 4, or may be provided with an adjustable or exchangeable closure. This allows the opening to be adjusted depending on the consistency of the patients stool. FIG. 5 shows an adjustable opening for the bottom of the plug. The closure can be formed integrally with the plug or as a separate closure, attaching to the plug in any suitable manner, such as mating threads. The bottom surface is provided with a semi-circular opening 77. A semicircular closure 78 is rotatably secured to the closure. By rotating closure 78, the amount of the semicircular opening 77 exposed can be adjusted.

Figure 6C:
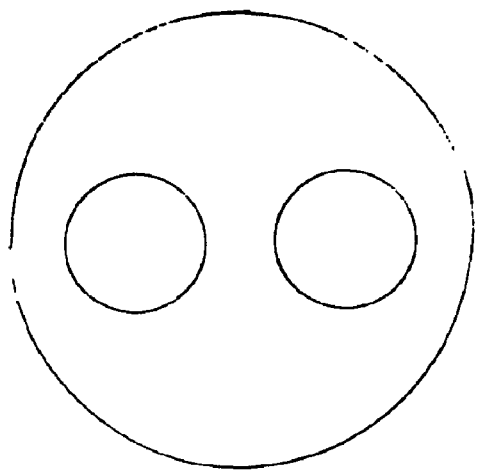
FIG. 6a-6c is a plan view of interchangeable ends for the plug.
Figure 6B:
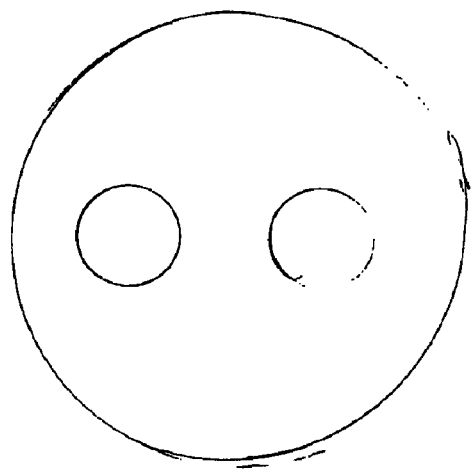
Figure 6A:
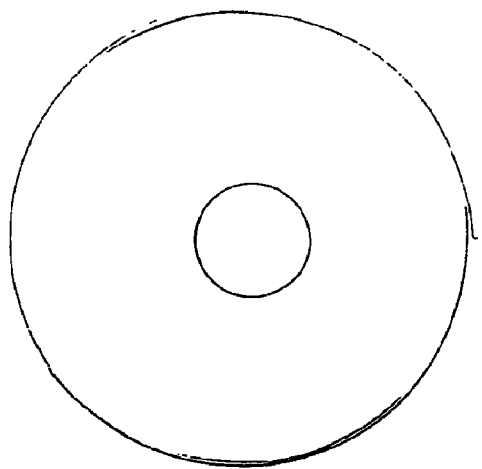

FIG. 6a-6c disclose exchangeable closures which may be attached to the bottom of the plug 14. The structure shown depicts FIG. 6a with a single small opening. FIG. 6b is shown with two small openings, whereas FIG. 6c has two larger openings. These three configurations are intended for a soft stool, medium stool and hard stool, respectively. Instead of being attachable, the plug may be formed with a bottom wall having the structure seen in FIG. 6a-6c. If integral, the plug having the appropriate sized openings is selected.

With the structure of the device being described, the operation may now be explained.

An absorbable sleeve 90 is fit about the plug 14. The plug 14 is then inserted into the central aperture 16. The plug may be frictionally fit or may have mating connectors to ensure the secure fit between the plug 14 and pad 12. When properly inserted, two electrical branches are created. In the embodiment shown, the first branch consists of the conductor 24, conductive ring 20, conductive ring 80, conductor 92 and conductor ring 102. The second branch consists of conductor 26, conductive ring 22, conductive ring 82, conductor 94 and conductive ring 100. When fecal matter passing through the intestines enters the hollow portion of the plug, and comes into physical contact with the lower conductive rings 100, 102, the two electrical branches just described complete a circuit. The completion of the circuit causes the circuit board 32 to activate alarm 38, which may be an Led 40. In addition, transmitter 44 can be used to cause a signal to be transmitted to a remote location, such as a nurses station. Also, vibrator 60 may be activated to provide the patient with a tactile warning. The alarm provides notice to the patient that a possible episode is eminent. The patient may then proceed to a bathroom to remove and empty the plug. After cleaning of the plug, the plug may be repositioned in the pad. The charcoal filter and ophobic filter allow gas to pass through the plug to eliminate bloating and provide comfort to the patient.

The device and method of the present invention provides incontinence that is controlled over intestinal gas and fecal matter, providing the user advance notice of a episode. The low profile of the device, when properly positioned, is virtually undetectable by others.

While the invention has been described with reference to a preferred embodiment, variations and modifications would be apparent to one of ordinary skill in the art. The invention encompasses such variations and modifications.

I claim:

1. An external alert device for detecting the presence of fecal matter comprising:
    an adhesive disposable pad having an aperture;
    a pH activated alarm attached to said pad;
    a first and second conductor extending from said aperture through said disposable pad to said alarm;
    a plug,
    a third and fourth conductor on said plug, said plug removably secured to said pad at said aperture wherein said third and fourth conductor each comprise a pair of spaced apart conductive rings.

2. The alert device of claim 1 wherein said alarm emits an audible alarm.

3. The alert device of claim 1 wherein said alarm emits a visible alarm.

4. The alert device of claim 1 wherein said alarm emits a tactile alarm.

5. The alert device of claim 1 wherein said alarm transmits a signal to a remote location.

6. The alert device of claim 1 wherein said plug is secured in said aperture by mating threads.

7. The alert device of claim 1 wherein said pad is a flexible, elastomeric material.

8. The alert device of claim 1 further comprising an inflatable cuff encircling said plug.

9. The alert device of claim 1 further including an absorbent sleeve disposed about said plug.

10. The alert device of claim 1 wherein said plug includes a filter.

11. The alert device of claim 1 further comprising an adhesive ring attached to one side of the pad.

12. The alert device of claim 1, wherein the third and fourth conductors each comprise
   a lower ring, an upper ring and an upwardly extending section extending between the upper and lower rings.

13. The alert device of claim 12, wherein the plug comprises a lumen having an outer surface and an inner surface,
   the upper ring extending about the outer surface and the lower ring extending about the inner surface.

14. The alert device of claim 12, wherein the first and second conductor each comprise a first section extending from a circuit board to the aperture and a ring extending around the aperture.

15. An external alert device for detecting the presence of fecal matter comprising:
   an adhesive pad having an aperture;
   a pH activated alarm attached to said pad;
   a first and second conductor extending from said aperture through said pad to said alarm;
   a plug,
   a third and fourth conductor on said plug, said plug removably secured to said pad at said aperture wherein said third and fourth conductor each comprise a pair of spaced apart conductive rings, wherein the first conductor is electrically connected to the third conductor and the second conductor is electrically connected to the fourth conductor when the plug is placed with in the aperture.

* * * * *